United States Patent [19]

Whistler

[11] Patent Number: 4,985,082
[45] Date of Patent: Jan. 15, 1991

[54] MICROPOROUS GRANULAR STARCH MATRIX COMPOSITIONS

[75] Inventor: Roy L. Whistler, West Lafayette, Ind.

[73] Assignee: Lafayette Applied Chemistry, Inc., West Lafayette, Ind.

[21] Appl. No.: 123,570

[22] Filed: Nov. 20, 1987

[51] Int. Cl.$^5$ .................... C08B 31/00; C08B 31/02; C08B 31/08
[52] U.S. Cl. ........................................ 127/33; 127/32; 536/102; 502/404; 252/315.3; 426/661; 435/202; 435/203; 435/204; 435/205
[58] Field of Search .................... 127/33, 32; 536/102; 435/202-205; 502/404; 252/315.3; 426/661

[56] References Cited

U.S. PATENT DOCUMENTS

| | | | |
|---|---|---|---|
| 3,922,197 | 11/1975 | Leach et al. | 435/202 |
| 3,922,198 | 11/1975 | Kuske et al. | 435/202 |
| 4,393,202 | 7/1983 | Breuninger | 127/67 |
| 4,551,177 | 11/1985 | Trubiano et al. | 127/32 |
| 4,585,858 | 4/1986 | Molotsky | 536/102 |

FOREIGN PATENT DOCUMENTS

| | | | |
|---|---|---|---|
| 8302955 | 9/1983 | PCT Int'l Appl. | 536/102 |
| 770089 | 3/1957 | United Kingdom | 536/102 |

OTHER PUBLICATIONS

"Scanning Electron Microscopy of Enzyme Digested Varagu Starch Granules", Paramahans, S. V. and Tharanathan, R. N., Starch/Starke, 34 (1982) Nr. 3, S. 73–76.
"Degradation of Starch Granules by Alpha-Amylase of Streptomyces precox NA-273", Takaya, T., Sugimoto, Y., Wako, K. and Fuwa, H., Starch/Starke, 31 (1979), Nr. 6, S. 205–208.
"Scanning Electron-Microscopy of Starch Granules with or without Amylase Attack", Fuwa, H., Sugimoto, Y., and Takaya, T.
"Susceptibility of Various Starch Granules to Amylases as Seen by Scanning Electron Microscope", Fuwa, H., Sugimoto, Y., Tanaka, M., Glover, D.V. Staerke 1979, 30(6), 186–191 (Abstract).
"Degradation of Various Starch Granules by Glucoamylases of Rhizopus Amagasakiens, Rhizopus Niveus, and Endomyces", Takaya, T., Glover, D.V., Sugimoto, Y., Tanaka M., Fuwa, H., Denpun Kagaku, 1982, 29(4), 287–293 (Abstract).
"Hydrolysis of Large and Small Starch Granules from Normal and Waxy Barley Cultivars by a-Amylases from Barley Malt", MacGregor, A. W., Ballance, D. L., Cereal Chem., 1980, 57(6), 397–402 (Abstract).
"Amyloglucosidase-Catalysed Erosion of Native, Surface-Modified and Chlorine-Treated Wheat Starch Granules. The Influence of Surface Protein", Greenwell, P., Evers, A. D., Gough, B. M., and Russell, P. L., Journal of Cereal Science, 3, (1985), 279–293 (Abstract).

Primary Examiner—Chung K. Pak
Attorney, Agent, or Firm—Barnes & Thornburg

[57] ABSTRACT

Amylase treated granular starches provide a microporous matrix material adapted for absorption and releasable containment of functional compositions. The microporous starch granules are chemically derivatized to enhance absorptive and structural properties. Absorbed functional substances are released from the microporous starch matrix under the influence of mechanical compression, by diffusion into a surrounding fluid or as a result of degradation of the granular starch matrix.

4 Claims, No Drawings

MICROPOROUS GRANULAR STARCH MATRIX COMPOSITIONS

BACKGROUND AND SUMMARY OF THE INVENTION

This invention relates to the processing of granular starch for use as a carrier for absorbed functional substances. More particularly, this invention provides a microporous granular starch matrix material useful for absorption and releasable containment of any of a wide variety of useful compositions. Absorbed compositions are released from the porous granular starch matrices by diffusion into surrounding fluids, by mechanical compression, or by chemical degradation of the starch matrix.

It has been known for quite a number of years that digestion of starch in food begins in the mouth on contact with salivary alpha-amylase. Starch digestion is completed in the duodenum of the small intestine where the starch granules come into contact with pancreatic alpha-amylyase and intestinal beta-amylase. Starch granules taken from the duodenum or natural starch granules that have been treated with alpha-amylase or glucoamylase in vitro for a period of time are noted under microscopic examination to have numerous holes or pores ranging over the entire surface. The number, size and depth of the pores depend upon the extent of the enzyme action. As normal digestion continues in the gastrointestinal tract the granule is entirely disintegrated by the alpha-amylase, by the normal beta-amylase of the intestine and by maltase which is also present.

In accordance with the present invention microporous starch granules are used as a carrier for a wide variety of functional substances. The granules are partially hydrolyzed with alpha-amylase and/or glucoamylase and optionally treated chemically to modify structural integrity and surface characteristics. The amylase-treated granules have numerous pores leading from the granule surface to the granule interior giving the treated granules a sponge-like appearance on microscopic examination. Substances can be readily absorbed into the porous granular starch matrix. That property also allows the present porous granular starches to find use as adjuvants for antiperspirants and as bulking agents for foods and drinks.

Use of granular starch matrices in accordance with the present invention allows for the preparation of new forms of art-recognized compounds and compositions having utility in the areas of food/nutrition, topical creams and lotions, cosmetics, agricultural products, and products for human and veterinary medicine. Such novel formulations can be designed to enhance or prolong the functional characteristics of absorbed compositions. For example, substances naturally of a liquid character can be formulated into a powder, paste or cream formulation, more easily adapted for packaging or for practical utility, such as for sustained release of said compositions.

DETAILED DESCRIPTION OF THE INVENTION

The starch matrix materials, in accordance with this invention, are prepared by treating granular starch, typically as a slurry in an aqueous medium, with a glucoamylase or alpha-amylase or a mixture of such enzymes, at temperatures below the gelatinization point of the starch. Enzyme treatment is continued until the granules have a pore volume of about 10% to about 40%, more preferably about 15% to about 25% of granule volume. Any of a wide variety of art-recognized alpha-amylases or glucoamylases including those derived from *Rhizopus niveus, Aspergillus niger*, and *Rhizopus oryzae* and *Bacillus subtilis* and alpha-amylases and glucoamylases of animal origin, can be used. The duration of enzyme treatment necessary to produce microporous starch granules for use in accordance with this invention depends on a number of variables, including the source of starch, species and concentration of amylases, treatment temperature, and pH of the starch slurry. The progress of starch hydrolysis can be followed by monitoring the D-glucose content of the reaction slurry. In a preferred embodiment, the starch hydrolysis reaction is allowed to proceed until about 17 to about 20% of the starch has been solubilized. Starch from any of a wide variety of starch-containing vegetable sources can be used to produce the starch matrices in accordance with this invention, however, economics favor the use of corn starch.

A wide range of pore sizes, granule firmness and structural stability can be produced simply by controlling the degree of starch hydrolysis. However, granular firmness and surface characteristics can be advantageously adjusted by further treatment of the microporous amylase treated starch granules. Although the partially hydrolyzed starch granules have been found to have surprising mechanical strength in the dry state and significant structural integrity in water dispersion, a greater degree of structural integrity can be introduced by treating the microporous granules with an effective amount of a bifunctional starch-reactive chemical cross-linking agent. Any of a variety of art-recognized starch cross-linking agents, including those recognized as food-acceptable by the Food and Drug Administration, can be used. Suitable cross-linking agents include phosphates such as sodium trimetaphosphate, dicarboxylic acids derivatives, particularly $C_2$-$C_6$ dicarboxylic acids including maleic and glutaric acid, phosphorous oxychloride, epichlorohydrin and $\beta,\beta$-dichlorodiethyl ether. Microporous starch granules become more and more resistant to mechanical damage and to swelling and dissolution with increased degree of cross-linking. Starch cross-linking agents are described in my book *Starch Chemistry And Technology*, second edition, 1984, Academic Press, Inc., New York, New York.

The capacity of microporous starch granules prepared in accordance with this invention to absorb functional substances is dependent upon the compatibility of the surfaces of the starch matrix with the intended absorbate. Thus, the partially hydrolyzed microporous granules can be treated with surface-modifying agents to enhance granule absorptivity. If the substance to be absorbed onto and into the starch matrix has a predominant lipid character, the starch matrix can be treated to render the pore surfaces more lipophilic. The partially hydrolyzed starch granules can be treated with solutions of synthetic polymers, such as methylcellulose, polyvinyl alcohol, poly-N-vinyl-2-pyrrolidone, polyacrylamide, carboxymethylcellulose, carragenan or other food grade gums. After such treatment, the granules, when dried, will take up liquids readily and will easily absorb fatty or lipid substances including oils and creams.

Alternatively absorbency for lipophilic substances can be facilitated by derivatizing starch molecules on the pore surfaces with long fatty acid chains, for example, by reacting the microporous granules with stearyl- or octenyl-succinic acid anhydride. The granule and pore surfaces are thereby rendered more lipophilic and more compatible with absorbates having a predominate lipid character. Absorbency of the granular starch matrices for lipophilic substances can also be enhanced by esterfying the partially hydrolyzed starch granules with long chain fatty acids or derivatives thereof, or by etherification with long chain fatty halides. Treatment with acetic anhydride will also provide some lipophilic character to the partially hydrolyzed granules but a higher level of derivatization is required.

The microporous granular starch matrices prepared in accordance with this invention can be utilized as an absorbent carrier for a wide range of functional substances. Exemplary of substances which can be absorbed into and on the partially hydrolyzed starch granules in accordance with this invention are salad oils, flavors, insect repellents, insecticides, herbicides, perfumes, moisturizers, soaps, waxes, body creams and lotions, vitamins and therapeutic drug substances. Such functional sorbates can be absorbed into the starch matrices of the present invention by either spraying solutions of such substances onto the prepared granular matrices or by adding the granular starch matrix material to solutions of said substances, separating the pore-loaded granules from solution by art-recognized techniques such as filtration or centrifugation and drying the substance bearing granules. The degree of loading of functional substances in the starch matrix can be controlled in part by adjusting the concentration of the functional substance in the solutions used to load the granular matrices. Higher matrix concentrations of the loaded material can be realized using more concentrated solutions of the substance and by repeating the loading procedure. Preferably the substances are absorbed into the starch matrix as their solutions in inert, relatively low boiling solvents which can be removed by evaporation following the absorption-loading of the starch matrix.

Compositions in accordance with the present invention comprising a starch matrix consisting essentially of amylase-treated starch granules having a microporous structure and a functional substance absorbed into said microporous structure can be used in powder form or it can be formulated into liquids, creams, tablets or other forms adapted to the intended usage of the absorbed functional substance. The absorbed substance is released from the microporous starch matrix either upon mechanical compression of the granular formulation or by chemical degradation of the starch matrix. Alternatively the granules can serve as a reservoir for the functional substance from which the substance is released to a surrounding medium simply by diffusion processes, thereby serving as a controlled or slow-release composition for said functional substance.

Microporous starches in accordances with this invention also find use as adjuvants for antiperspirants and as metabolizable bulking agents (i.e., to provide a pulpy texture) to foods and drinks. For that later use the microporous starches can be employed in a cross-linked form utilizing any one of the cross-linking agents herein described, or they can be employed without further chemical modificaion. For many applications the cross-linked material in the diester phosphate form at the levels of 0.1-0.5% are quite satisfactory.

The following examples are presented to illustrate the present invention and should not in any way be construed as a limitation thereof.

EXAMPLE 1

Ten grams of corn starch in 100 milliliters of water was treated with glucoamylase (Zymetec GA-200) from *Aspergillus niger* for 15 hours at 25° and pH 4.2. The slurry was filtered. The enzyme-treated granular starch was washed and could be used at once to take up flavors and creams and other ingredients. It has been found desirable to stop the enzyme hydrolysis reaction after dissolution of 17-20% of the starch, as can be determined by standard reducing value measurement of the supernatant of the reaction mixture.

A portion of the isolated starch granules was washed with a 0.5% solution of methylcellulose to make it more compatible with lipophilic sorbates. Another portion was dried for later use in absorption of body cream and after shave cream.

Another portion of the partially hydrolyzed starch was treated in water with stirring with 0.1% phosphorus oxychloride, phosphoryl trichloride, in an amount of 0.5 to 0.4% and warmed to 35° while at a pH of 8 to 12 for one hour to cross-link the starch molecules to a small degree. The cross-linked starch granules were washed, filtered and dried for future use in taking up sorbates.

It was found that a very low degree of cross-linking does well to strengthen the porous granule Thus, 100 grams of porous starch in 250 milliliters of water at pH 10.0, adjusted with 1.0N. sodium hydroxide, was stirred slowly during 45 minutes while 50 microliters of phosphoryl chloride dissolved in four milliliters of carbon tetrachloride was slowly added. The pH was maintained over this period by addition of sodium hydroxide solution and then adjusted with dilute (about 1N.) hydrochloric acid to pH 5.5. The slurry was centrifuged, and the precipitated starch derivative washed with water and again centrifuged. This washing was repeated twice more and the starch was finally dried under at 35° in a current of air.

EXAMPLE 2

Twenty grams of dasheen starch in 100 milliliters of water was hydrolyzed with commercial alpha-amylase (enzyme to substrate ratio 1:66) at pH 5.5 and 30° C. for 20 hours with slow stirring. The dispersion was then filtered and washed first with water and then with isopropanol and dried at room temperature (about 25° C.). When these granules were examined microscopically in glycerol-water (ratio 1:1) they showed numerous deep pores distributed over the granules. When some granules were sprinkled as a powder on double sided Scotch tape and shadowed in a vacuum with gold and examined in a scanning electron microscope (JMS-840, JEOL), the granules were seen to have numerous deep pores distributed throughout.

EXAMPLE 3

Ten grams of wheat starch was treated with temperature sensitive *Bacillus subtilis* alpha-amylase in a 100 milliliter solution of sodium acetate-acetic acid buffer at pH 4.7 and 30° for 6 hours, filtered and washed with water, dried and heated to inactivate the enzyme. The product was used as such or was washed with 0.1% methylcellulose or polyvinyl alcohol solution of 0.1% and dried or was cross-linked with phosphoryl chloride as stated above and dried.

EXAMPLE 4

Ten grams of potato starch in 50 milliliters of a solution of sodium acetate-acetic acid buffer at pH 4.7 was treated with glucoamylase at 30° for 2.5 hours, filtered and washed with water and product subjected to moderate cross-linking using the conditions described in U.S. Pat. No. 2,328,537, Sept. 7, 1944 by George E. Felton and Herman H. Schopmeyer of the American Maize-Products Company. The conditions were adjusted so as to introduce a degree of substitution of 0.01 to 0.5.

EXAMPLE 5

Starch granules were hydrolyzed as in Example 2 above, and the freshly washed product was treated under mild alkaline conditions, about pH 9, with maleic anhydride. The dried product was heated to 100° for 30 minutes to effect a partial Michael condensation and partial cross-linking by way of the carboxyl groups forming ester linkages with hydroxyl groups on the adjacent starch molecules. The partially hydrolyzed starch granules can also be cross-linked with a variety of reagents and by methods referred to in my book *Starch Chemistry and Technology* referred to above.

EXAMPLE 6

Cassava (tapioca) starch was hydrolyzed with glucoamylase for 6 hours at 30° and pH 5 and the pH of the solution was adjusted to 10.5 by the addition of 3.5% sodium carbonate. Sodium trimetaphosphate was added to a concentration of 2% by weight and the reaction mixture was heated to 50° C. for 1.5 to 2 hours. (Sodium trimetaphosphate is readily available but can be made by heating sodium dihydrogen orthophosphate at 550° C. for 2 hours.) At the end of the reaction the starch slurry is washed with water until the washings are free of reagents and then adjusted to pH 6.5 with hydrochloric acid. The starch product is filtered and dried at 40° C.

EXAMPLE 7

Ten grams of commercial corn starch, pearl starch, in 100 milliliters of water at pH 5.0 was treated at 25° C. for 8 hours with equal amounts of alpha-amylase and glucoamylase in the ratio of starch substrate to total enzyme of 66:1 and the mixture was allowed to stand at 8° C. for 16 additional hours with gentle shaking. The resulting starch granules observed microscopically were seen to have slightly greater Porosity than those treated with either enzyme alone. This might suggest that a shorter reaction time could be employed if mixed enzymes were used. However, commercial amylase and glucoamylase enzymes are known not to be pure and may contain a little of one type when the other type is prepared for commercial customers.

What is claimed is:

1. A starch matrix material for releasable containment of an absorbate, said matrix material comprising starch granules partially hydrolyzed with amylase in an aqueous medium at a temperature below the gelatinization point of said granules to produce microporous starch granules, said microporous starch granules being additionally contacted with a solution of a surface modifying agent effective to enhance compatibility of the surfaces of said microporous starch granules with said absorbate, the surface modifying agent being selected from the group consisting of methylcellulose, carboxymethylcellulose, polyvinyl alcohol, poly-N-vinyl-2-pyrrolidone, polyacrylamide, a starch reactive etherifying agent and a starch reactive esterifying agent.

2. The starch matrix material of claim 1 wherein the starch reactive agents are selected from the group consisting of stearylsuccinic acid anhydride, acetic anhydride and octenylsuccinic acid anhydride.

3. The starch matrix material of claim 1 wherein, in addition to treatment with said surface modifying agent, the microporous granules are reacted with an effective amount of a bifunctional starch reactive chemical cross-linking agent to enhance the rigidity and structural integrity of said microporous granules.

4. The crosslinked microporous starch matrix material of claim 3 wherein the crosslinking agent is selected from phosphorous oxychloride, epichlorohydrin sodium trimetaphosphate, $C_2$-$C_6$ dicarboxylic acids, and $\beta,\beta$-dichlorodiethyl ether.

* * * * *